(12) United States Patent
Nakazawa et al.

(10) Patent No.: US 9,086,491 B2
(45) Date of Patent: Jul. 21, 2015

(54) RADIATION TOMOGRAPHY APPARATUS

(75) Inventors: Masayuki Nakazawa, Kyoto (JP);
Junichi Ohi, Muko (JP); Tetsuo Furumiya, Shiga (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/346,658

(22) PCT Filed: Sep. 22, 2011

(86) PCT No.: PCT/JP2011/005352
§ 371 (c)(1),
(2), (4) Date: Mar. 21, 2014

(87) PCT Pub. No.: WO2013/042173
PCT Pub. Date: Mar. 28, 2013

(65) Prior Publication Data
US 2014/0239184 A1 Aug. 28, 2014

(51) Int. Cl.
*G01T 1/20* (2006.01)
*G01T 1/164* (2006.01)
*G01T 1/29* (2006.01)

(52) U.S. Cl.
CPC ............ *G01T 1/164* (2013.01); *G01T 1/2006* (2013.01); *G01T 1/2985* (2013.01)

(58) Field of Classification Search
CPC ......... G01T 1/164; G01T 1/20; G01T 1/2006; G01T 1/2985
USPC ....................................................... 250/366
See application file for complete search history.

(56) References Cited

U.S. PATENT DOCUMENTS

| 2010/0027866 A1 | 2/2010 | Ohi |
| 2010/0127179 A1 | 5/2010 | Tonami et al. |

FOREIGN PATENT DOCUMENTS

| CN | 101460864 A | 6/2009 |
| CN | 101563627 A | 10/2009 |
| JP | 2008-089384 A | 4/2008 |
| JP | 2008-190901 A | 8/2008 |
| WO | 2007/015198 A2 | 2/2007 |

OTHER PUBLICATIONS

International Search Report, w/ English translation thereof, issued in International Application No. PCT/JP2011/005352 dated Dec. 20, 2011.
Supplementary European Search Report EP Application No. 11872804.7 dated Feb. 27, 2015.

*Primary Examiner* — David Porta
*Assistant Examiner* — Gisselle Gutierrez
(74) *Attorney, Agent, or Firm* — McDermott Will & Emery LLP

(57) ABSTRACT

The disclosure has one object to provide a radiation tomography apparatus of a low price that facilitates a design change of a detector ring to suppress costs of development. The radiation tomography apparatus according to the disclosure includes a plurality of modules configured to receive detected data from different radiation detectors. Then, the modules each send and receive the detected data to and from one another, thereby sharing the detected data and counting the number of coincidence events. That is, when manufacturing radiation tomography apparatus, merely wiring the coincidence modules achieves implementation of the coincidence unit. This allows manufacturing the radiation tomography apparatus without new development of a substrate for performing coincidence. Consequently, the radiation tomography apparatus of a low price can be provided with suppressed costs of the development.

7 Claims, 4 Drawing Sheets

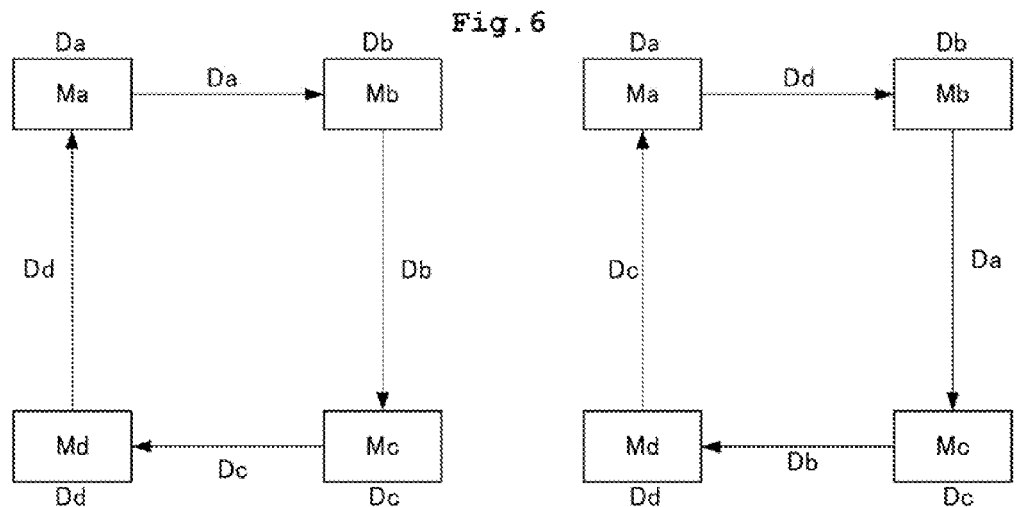
Fig.6
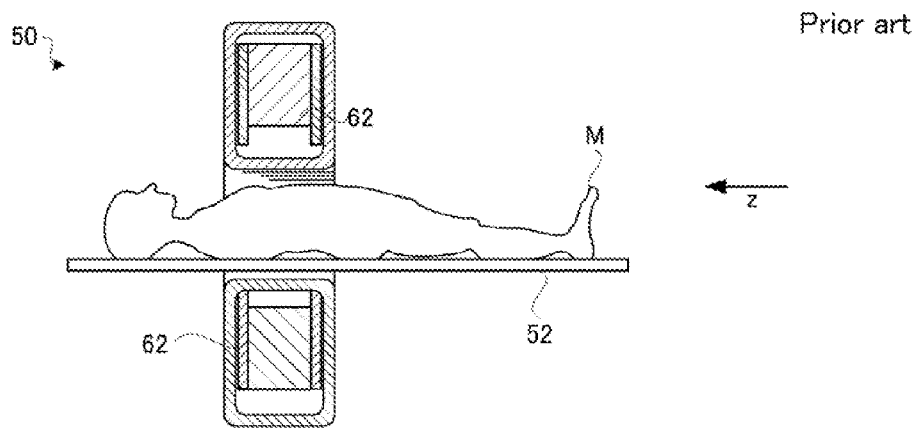
Fig.7 — Prior art
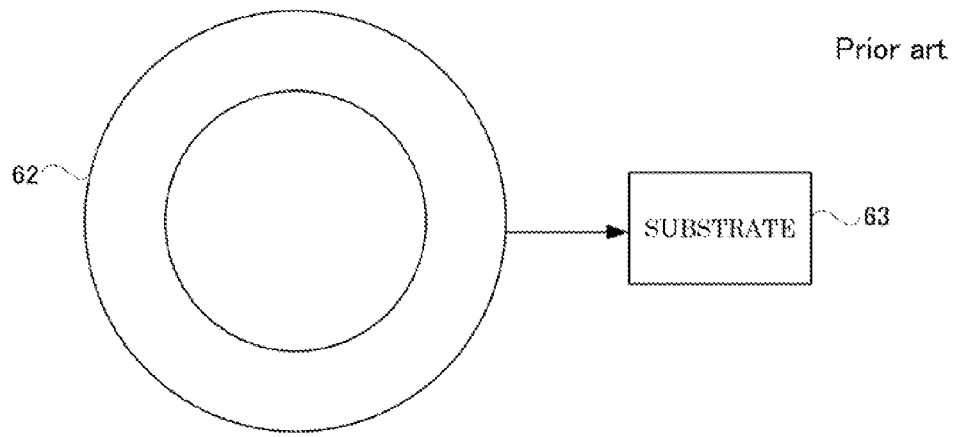
Fig.8 — Prior art

RADIATION TOMOGRAPHY APPARATUS

RELATED APPLICATION

This application is the U.S. National Phase under 35 U.S.C. §371 of International Application No. PCT/JP2011/005352, filed on Sep. 22, 2011, the disclosure of which Application is incorporated by reference herein.

TECHNICAL FIELD

The present invention relates to a radiation tomography apparatus that images radiation emitted from a subject. In particular, the present invention is directed to a radiation tomography apparatus that generates a tomographic image through performing coincidence.

BACKGROUND ART

Description will be given of a concrete construction of a conventional radiation tomography apparatus. As illustrated in FIG. 7, a conventional radiation tomography apparatus 50 includes a top board 52 configured to support a subject M placed thereon, and a detector ring 62 configured to detect annihilation radiation pairs. The detector ring 62 has an opening into which the subject M is insertable together with the top board 52.

When the conventional radiation tomography apparatus 50 is used to determine radiopharmaceutical distribution in the subject M, the subject M is moved inside the opening of the detector ring 62. Thereafter, positions of occurrence of annihilation radiation-pairs emitted from the subject M are imaged, whereby a radiation tomographic image is obtained. Such a radiation tomography apparatus is referred to as a PET (positron emission tomography) apparatus. The PET apparatus identifies occurrence status of the annihilation radiation-pairs by counting the number of coincidence events, thereby obtaining a tomographic image. Here, the coincidence event represents detection of two rays of radiation at different positions in the detector ring 62.

The detector ring 62 has radiation detectors arranged annularly. Consequently, an annihilation radiation-pair is detected coincidentally with different radiation detectors. Each of the radiation detectors cannot determine whether or not the detected radiation is derived from the annihilation radiation-pair. Accordingly, the conventional construction transmits the detected data received from the radiation detectors to one substrate 63. See FIG. 8. The substrate 63 receives the detected data from all the radiation detectors constituting the detector ring 62. The substrate 63 finds two pieces of the detected data having coincident detection time. In such manner, one coincidence event is to be found.

The substrate 63 successively finds coincidence events through checking the detected data, and counts the number of coincidence events. The number of coincidence events obtained in such manner is used for generating a tomographic image. See, for example, Japanese Patent Publication No. 2008-190901A.

PATENT LITERATURE

Patent Literature 1 Japanese Patent Publication No. 2008-190901A

SUMMARY OF INVENTION

Technical Problem

However, the conventional construction has the following drawback. Specifically, the conventional construction has difficulty in changing an apparatus design. As illustrated in FIG. 8, the conventional construction includes one substrate 63 for the detector ring 62, the substrate 63 counting the number of coincidence events. The number of radiation detectors constituting the detector ring 62 is variable depending on purposes of the apparatus. For instance, a radiation tomography apparatus for imaging a whole body of a subject includes a detector ring 62 with approximately one hundred radiation detectors being arranged annularly. Moreover, a radiation tomography apparatus for animal experiment includes a detector ring 62 with approximately eight radiation detectors being arranged annularly.

The conventional construction needs to prepare one substrate 63 for counting the number of coincidence events for the detector ring 62. Consequently, upon development of a new radiation tomography apparatus, it may be necessary to redesign the substrate 63 for counting the number of coincidence events. It is assumed, for example, that a new radiation tomography apparatus is to be developed having the detector ring constituted by fifty radiation detectors arranged annularly. In addition, it is also assumed that such the detector ring has not been manufactured. The conventional construction needs to prepare a new substrate 63 that allows counting the number of coincidence events in the fifty radiation detectors. This is because no substrate 63 corresponding to such the detector ring has been designed yet.

In other words, with the conventional construction, the substrates 63 adaptable to the number of radiation detectors may be necessarily produced newly upon the development of the radiation tomography apparatus. Such the circumstance contributes to increase in cost of the development of the radiation tomography apparatus.

The present invention has been made regarding the state of the art noted above, and its one object is to provide a radiation tomography apparatus of a low price that facilitates a design change of a detector ring to suppress costs of development.

Solution to Problem

The present invention adopts the following construction for overcoming the above drawback. That is, one aspect of the present invention discloses a radiation tomography apparatus including a plurality of radiation detectors, and a plurality of modules. The modules are connected to the radiation detectors respectively, and are connected to one another to send and receive detected data outputted from the radiation detectors mutually, thereby sharing the detected data and counting the number of coincidence events.

Operation and Effect

The radiation tomography apparatus according to the aspect of the present invention includes a plurality of modules configured to receive the detected data from the different radiation detectors. Then, the modules each send and receive the detected data mutually, thereby sharing the detected data and counting the number of coincidence events. In other words, a plurality of modules cooperates to function as a coincidence device that counts the number of coincidence events. That is, when manufacturing radiation tomography apparatus, merely wiring the coincidence modules achieves implementation of the coincidence unit. This allows manufacturing the radiation tomography apparatus without new development of the substrate for performing coincidence. Consequently, the radiation tomography apparatus of a low price can be provided with suppressed costs of the development.

Moreover, it is more desirable that the modules of the radiation tomography apparatus are provided in the radiation detectors respectively.

Operation and Effect

The above construction is a more detailed construction of the radiation tomography apparatus according to the present invention. The modules are provided in the radiation detectors respectively so as to correspond to the radiation detectors in a one-to-one manner. This ensures to divide a function of the coincidence device.

Moreover, the radiation tomography apparatus further includes a clock configured to send time information to the modules collectively, and the modules determine a coincidence property of the detected data in accordance with the time information received from the clock. Such is more desirable.

Operation and Effect

The above construction is a more detailed construction of the radiation tomography apparatus according to the present invention. Each of the modules determines the coincidence property of the detected data in accordance with the time information received from the clock. This allows performance coincidence accurately in accordance with the time information with more accuracy.

Moreover, the radiation tomography apparatus includes a control information setting device configured to send control information on coincidence to each of the modules collectively, and the modules operate in accordance with the control information received from the control information setting device. Such is more desirable.

Operation and Effect

The above construction is a more detailed construction of the radiation tomography apparatus according to the present invention. The modules each operate in accordance with the control information received from the control information setting device collectively. This allows immediate reflection of changing the control information to the coincidence device.

Moreover, in the radiation tomography apparatus, the detection data is sent from one to the other of two modules among the modules, the two modules corresponding to the radiation detectors adjacent to each other in the detector ring constituted by the radiation detectors arranged annularly, and the detected data is similarly sent and received repeatedly, whereby the detected data received from one of the radiation detector is sent to one of the modules corresponding to the radiation detector located half the detector ring away. Such is more desirable.

Operation and Effect

The above construction is a more detailed construction of the radiation tomography apparatus according to the present invention. The detected data received from a radiation detector corresponding to a module is sent up to a module corresponding to a radiation detector located half the detector ring away. This allows more accurate performance of coincidence to the modules.

Moreover, it is more desirable that the radiation tomography apparatus is used for whole-body subject imaging, breast imaging, or small animal imaging.

Operation and Effect

The above construction is a more detailed construction of the radiation tomography apparatus according to the present invention. The number of radiation detectors constituting the detector ring is variable among the constructions of such the apparatus. However, the embodiment of the present invention can achieve a coincidence device by merely wiring the modules. This causes unnecessary development of a new substrate performing coincidence.

Advantageous Effects of Invention

The radiation tomography apparatus according to the embodiment of the present invention includes a plurality of modules receiving detected data from different radiation detectors, respectively. Then, the modules each send and receive the detected data mutually, thereby sharing the detected data and counting the number of coincidence events. That is, when manufacturing radiation tomography apparatus, merely wiring the coincidence modules achieves implementation of the coincidence unit. This allows manufacturing the radiation tomography apparatus without new development of the substrate for coincidence. Consequently, the radiation tomography apparatus of a low price can be provided with suppressed costs of the development.

BRIEF DESCRIPTION OF DRAWINGS

FIGS. 5 and 6 are schematic views each illustrating operation of a coincidence module according to the embodiment.

FIG. 7 is a sectional view illustrating a conventional radiation tomography apparatus.

FIG. 8 is a schematic view illustrating the conventional radiation tomography apparatus.

DESCRIPTION OF EMBODIMENTS

Description will be given of embodiments of the present invention with reference to drawings.

Embodiment 1

<Construction of Radiation Tomography Apparatus>

Figure 1:
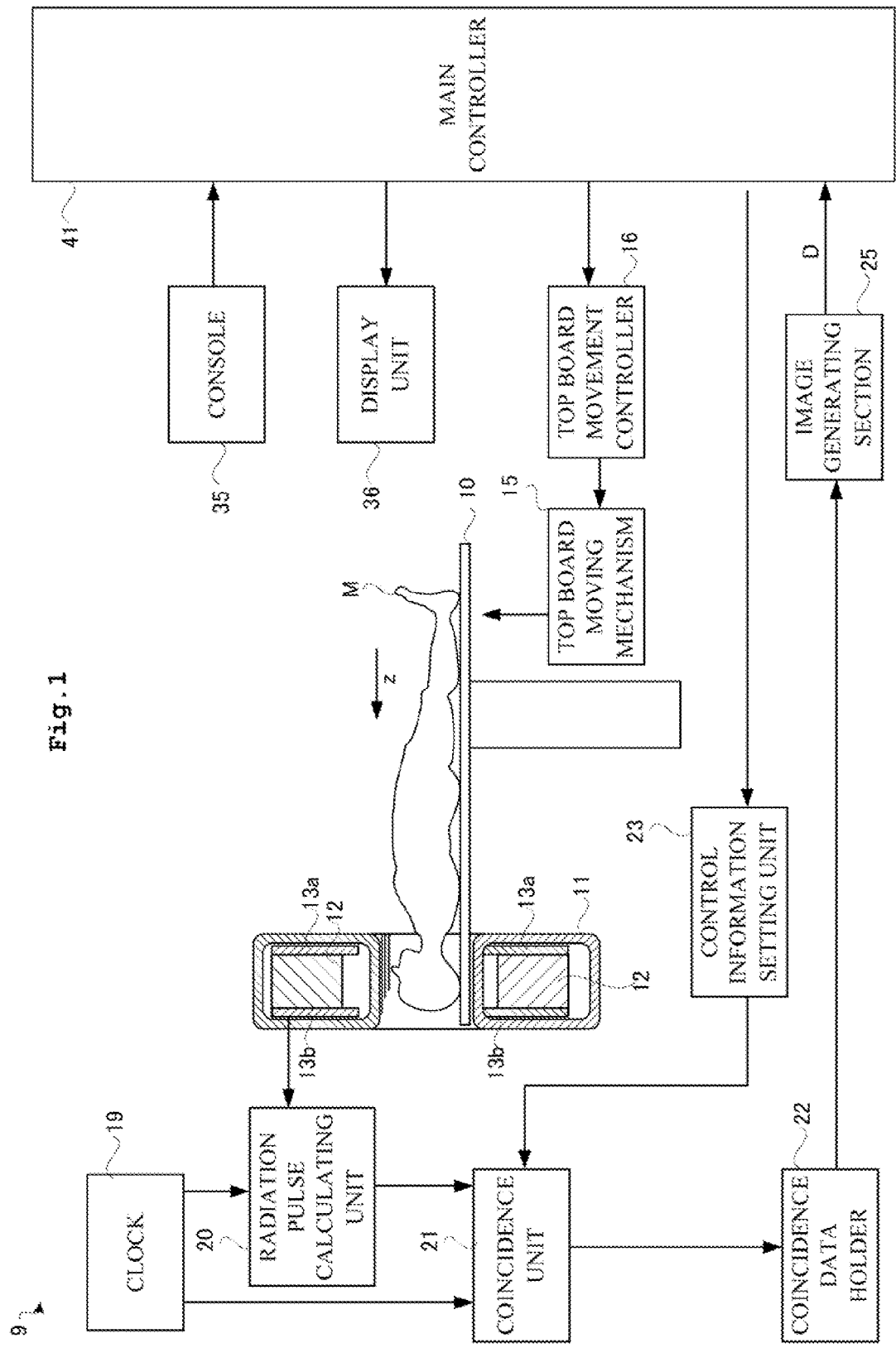
FIG. 1 is a function block diagram illustrating a radiation tomography apparatus according to one embodiment of the present invention.

Description will be given hereinunder of a radiation tomography apparatus 9 according to one embodiment of the present invention with reference to drawings. FIG. 1 is a function block diagram illustrating the radiation tomography apparatus 9 according to Embodiment 1. The radiation tomography apparatus 9 according to Embodiment 1 is used for whole-body imaging. The radiation tomography apparatus 9 includes a top board 10 configured to support a subject M placed thereon, a gantry 11 with an opening through which the top board 10 is guided in a longitudinal direction (z-direction) of the top board 10, and a detector ring 12 in a ring shape provided inside the gantry 11 and configured to guide the top board 10 in the z-direction. The opening of the detector ring 12 is cylindrical extending in the z-direction (the longitudinal direction of the top board 10, i.e., a body-axis direction of the subject M). Accordingly, the detector ring 12 itself extends in the z-direction. The gantry 11 has the opening sufficient for accommodating the subject M, into which the subject M is to be inserted.

The top board 10 can pass through the opening of the gantry 11 (detector ring 12) in the z-direction, and is movable forward and backward in the z-direction. A top board moving mechanism 15 slides the top board 10 as above. A top board movement controller 16 controls the top board moving mechanism 15. The top board movement controller 16 is a top board movement control device for controlling the top board moving mechanism 15. The top board 10 slides from outside the detector ring 12 in its entirety, and one end of the top board 10 is guided into the opening of the detector ring 12.

The detector ring 12 is provided inside the gantry 11 for detecting annihilation γ-ray pairs emitted from the subject M. The detector ring 12 has a cylindrical shape extending in the body-axis direction of the subject M, and has a length of approximately 15 cm to 26 cm. Ring absorbers 13a, 13b cover both ends of the detector ring 12 in a central axis direction (z-direction). The absorbers 13a, 13b are made of a material metal having difficulty in passing through γ-rays, thereby preventing γ-rays to enter externally into the detector ring 12. The absorbers 13a, 13b remove γ-rays, obstructive for imaging a tomographic image D of the subject M, that are generated outside the detector ring 12. The absorbers 13a, 13b each have an internal diameter smaller than that of the detector ring 12.

Figure 2:
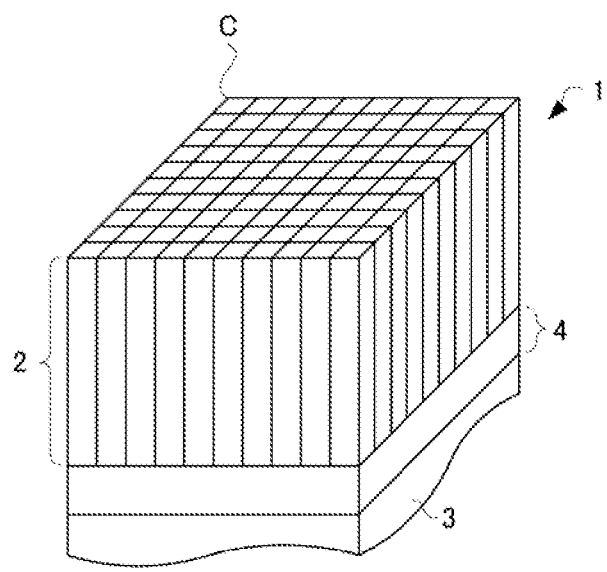
FIG. 2 is a perspective view illustrating a radiation detector according to the embodiment.

Description will be given next of the radiation detector 1 constituting the detector ring 12. FIG. 2 is a perspective view illustrating the radiation detector according to Embodiment 1. As illustrated in FIG. 2, the radiation detector 1 includes a scintillator 2 configured to convert γ-rays into fluorescence, and a light detector 3 configured to detect the fluorescence. Moreover, a light guide 4 configured to transmit the fluorescence is disposed between the scintillator 2 and the light detector 3.

The scintillator 2 has scintillation counter crystals arranged two-dimensionally. Each of the scintillation counter crystals C is composed of Ce-doped $Lu_{2(1-X)}Y_{2X}SiO_5$ (hereinafter referred to as LYSO). The light detector 3 allows determination of an occurrence position of fluorescence about which scintillation counter crystal emits fluorescence as well as about intensity of the fluorescence and time when the fluorescence is generated. The radiation detector 1 determines energy of the detected γ-rays from the intensity of the fluorescence, thereby allowing output of data on the energy. Here, the scintillator 2 having the configuration of Embodiment 1 is only exemplification of an aspect that may be adopted. Consequently, the configuration of the present invention is not limited to this.

Figure 3:
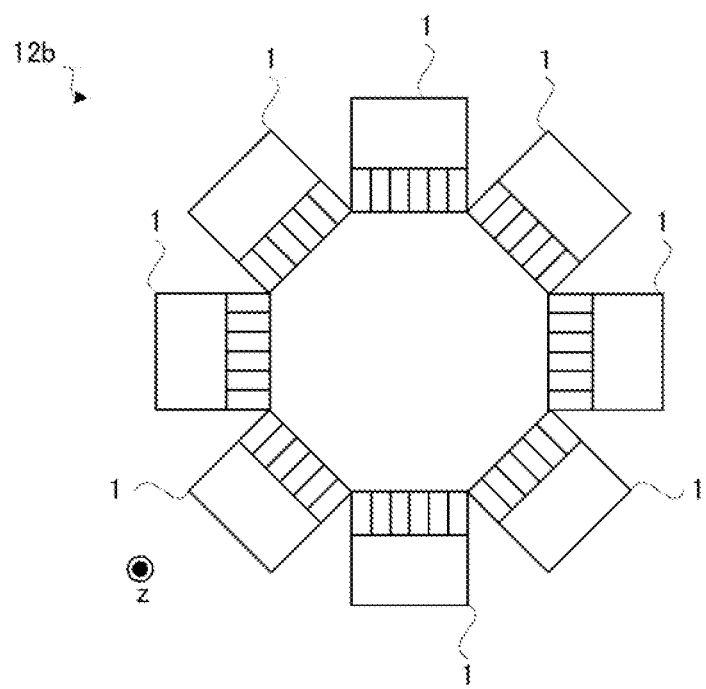
FIG. 3 is a plan view illustrating a detector ring according to the embodiment.

Description will be given of the detector ring 12. As illustrated in FIG. 3 of Embodiment 1, a plurality of radiation detectors 1 is arranged in a virtual circle on a plane orthogonal to the z-direction to form a unit ring 12b. A plurality of unit rings 12b is arranged in the central-axis direction (z-direction) to form the detector ring 12.

A clock 19 sends time information with serial numbers to a coincidence unit 21. A control information setting unit 23 sends information (control information) on control of the coincidence unit 21 to the coincidence unit 21. The coincidence unit 21 is to operate in accordance with the control information. The control information is a set value, such as a time window and an energy window, referred to upon determination of the coincidence property. The coincidence unit 21 corresponds to the coincidence device in the present invention. The control information setting unit 23 corresponds to the control information setting device in the present invention.

A radiation pulse calculating unit 20 identifies a position where the detector ring 12 detected γ-rays. Then, information on the detected position identified by the radiation pulse calculating unit 20 is sent to the coincidence unit 21. The radiation pulse calculating unit 20 obtains energy of incident γ-rays in addition to the detected position.

The coincidence unit 21 receives detected data from the radiation pulse calculating unit 20. It is conceivable that two γ-rays entering in the detector ring 12 coincidentally is an annihilation γ-ray pair derived from the radiopharmaceutical in the subject. The coincidence unit 21 counts frequency of detecting the annihilation gamma-ray pair entering coincidentally for every combination of two scintillation counter crystals constituting the detector ring 12, and the resultant is sent to a coincidence data holder 22. Counting the number of γ-rays entering coincidentally is referred to as coincidence. Here, the coincidence unit 21 uses the time information that the clock 19 gives to the detected data for determining the coincident property of the detected data. In such manner, the coincidence unit 21 counts the number of coincidence events that radiation enters coincidentally into two of the radiation detectors 1 constituting the detector ring 12.

Figure 4:
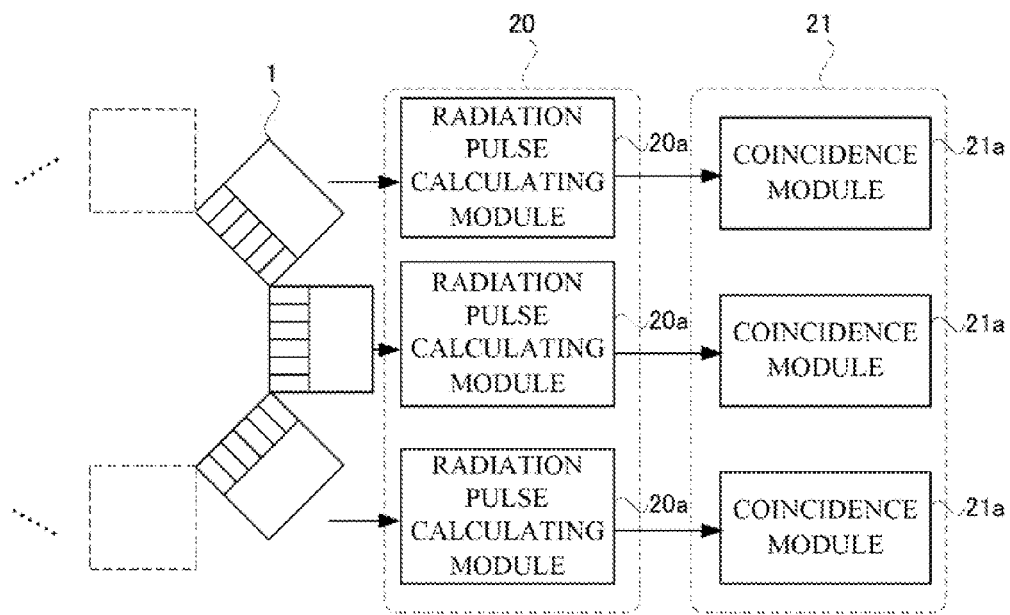
FIG. 4 is a schematic view illustrating a coincidence unit according to the embodiment.

Description will be given of the radiation pulse calculating unit 20 with FIG. 4. As illustrated in FIG. 4, the radiation pulse calculating unit 20 is constituted by radiation pulse calculating modules 20a provided in the radiation detectors 1, respectively. The radiation detectors 1 constitute the detector ring 12. The radiation pulse calculating modules 20a are connected to the radiation detectors 1 in a one-to-one manner. Accordingly, the radiation pulse calculating modules 20a are prepared to all the radiation detectors. In addition, each of the radiation pulse calculating modules 20a stores data (positional detector data) representing a position of the radiation detector corresponding to the radiation pulse calculating module 20a in the detector ring 12. The radiation pulse calculating modules 20a each store different types of detector positional data. This is because the radiation detectors 1 are located in different positions in the detector ring 12.

Description will be given next of the coincidence unit 21 with FIG. 4. As illustrated in FIG. 4, the coincidence unit 21 is constituted by coincidence modules 21a each provided in the radiation pulse calculating modules 20a respectively. The coincidence modules 21a are connected to the radiation pulse calculating modules 20a in a one-to-one manner. Accordingly, the coincidence modules 21a are connected to all the radiation detectors 1 in a one-to-one manner. That is, one module 21a obtains detected data from one radiation detector corresponding thereto (specifically, detected data is obtained through one radiation pulse calculating module 20a). Moreover, another coincidence module 21a obtains detected data from another radiation detector corresponding thereto (specifically, detected data is obtained through another radiation pulse calculating module 20a). The coincidence module 21a corresponds to the module in the present invention.

Description will be given of operation of the position identifying unit 20. When detecting γ-rays, the radiation detector 1 sends original signals concerning γ-ray detection to the corresponding radiation pulse calculating module 20a. The radiation pulse calculating module 20a identifies an incident position in the radiation detector 1 where the γ-rays enter in accordance with the original signals. Thereafter, the radiation pulse calculating module 20a identifies which position in the detector ring 12 corresponds to the presently identified incident position. The position in the detector ring 12 is identified with the detector positional data. Finally, the radiation pulse calculating module 20a outputs the detected data to the coincidence unit 21.

Description will be given next of operation of the coincidence unit 21. When receiving the detected data from the radiation pulse calculating module 20a corresponding to the coincidence module 21a, the coincidence module 21a applies time information with reference to time information from the clock 19. Thereafter, coincidence is performed with the detected data to which the time information has been applied.

The coincidence module 21a is also connected to another coincidence module 21a, and accordingly, the detected data with the applied time information is sent to the other coincidence module 21a. In such manner, the coincidence modules 21a each send and receive the detected data to and from one another, thereby sharing the detected data and performing coincidence.

Figure 5:
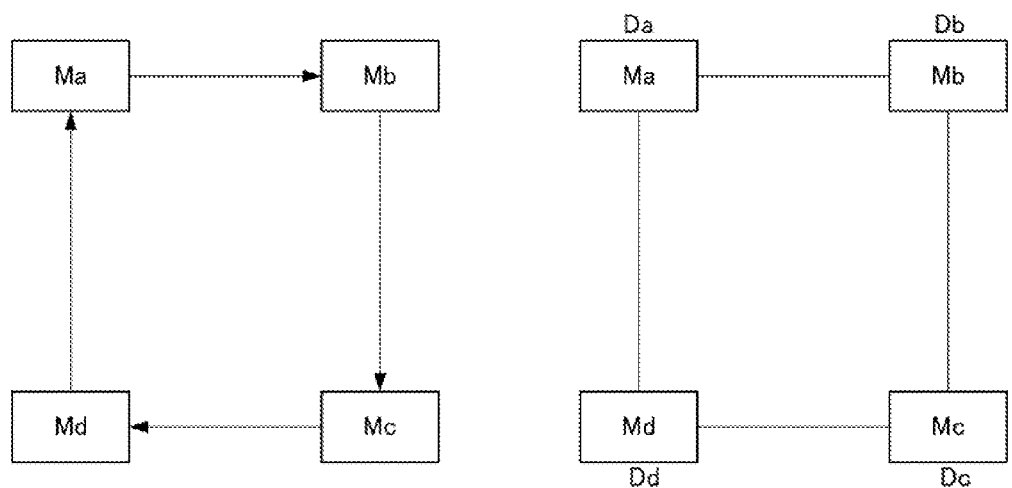

FIG. 5 illustrates sending and receiving of the detected data among the coincidence modules 21a. For simple explanation, it is assumed that the coincidence unit 21 is constituted by four coincidence modules 21a. FIG. 5 illustrates on the left thereof four coincidence module Ma, Mb, Mc, Md based on the positions of the radiation detectors. In FIG. 5, the coincidence modules Ma, Mb, Mc, Md are each arranged clockwisely.

Description will be given of operation of the coincidence modules Ma, Mb, Mc, and Md. As illustrated in FIG. 5 on the left thereof, the coincidence modules Ma, Mb, Mc, and Md send the detected data clockwisely. Specifically, the coincidence module Ma sends the detected data to the coincidence module Mb, and the coincidence module Mb sends the detected data to the coincidence module Mc. Then, the coincidence module Mc sends the detected data to the coincidence module Md, and the coincidence module Md sends the detected data to the coincidence module Ma. Here, clockwise sending is performed for expediency of explanation. Alternatively, counterclockwise sending may be performed.

FIG. 5 on the right thereof illustrates the coincidence modules Ma, Mb, Mc, and Md having received the detected data from the corresponding radiation pulse calculating modules 20a. In other words, sending and receiving of the detected data is not performed among the coincidence modules in this state. Here, the detected data that the coincidence module Ma receives from the radiation pulse calculating module 20a is expressed as detected data Da, the detected data that the coincidence module Mb receives from the radiation pulse calculating module 20a is expressed as detected data Db. Moreover, the detected data that the coincidence module Mc receives from the radiation pulse calculating module 20a is expressed as detected data Dc, and the detected data that the coincidence module Md receives from the radiation pulse calculating module 20a is expressed as detected data Dd.

FIG. 6 illustrates sending and receiving the detected data Da, Db, Dc, Dd of the detected data among the coincidence modules Ma, Mb, Mc, Md. Firstly, as illustrated on the left of FIG. 6, the coincidence module Ma sends the detected data Da to the coincidence module Mb, and the coincidence module Mb sends the detected data Db to the coincidence module Mc. Then, the coincidence module Mc sends the detected data Dc to the coincidence module Md, and the coincidence module Md sends the detected data Dd to the coincidence module Ma.

At the time when such sending has been performed (see the left of FIG. 6), the coincidence module Ma holds the detected data Da besides the detected data Dd from the coincidence module Md. Consequently, the coincidence module Ma allows performing coincidence to the detected data Dd, Da. This achieves counting the number of annihilation γ-ray pairs entering in two radiation detectors corresponding to the coincidence modules Md, Ma.

Similarly, at the time when such sending has been performed (see the left of FIG. 6), the coincidence module Mb holds the detected data Db besides the detected data Da from the coincidence module Ma. In addition, the coincidence module Mc holds the detected data Dc besides the detected data Db from the coincidence module Mb. The coincidence module Md holds the detected data Dd besides the detected data Dc from the coincidence module Mc.

Accordingly, at the time when such sending has been performed (see the left of FIG. 6), the coincidence module Mb allows performing coincidence to the detected data Da, Db, and the coincidence module Mc allows performing coincidence to the detected data Db, Dc. Moreover, the coincidence module Md allows performing coincidence to the detected data Dc, Dd.

Thereafter, as illustrated in the right of FIG. 6, the coincidence module Ma sends the detected data Dd to the coincidence module Mb, and the coincidence module Mb sends the detected data Da to the coincidence module Mc. Then, the coincidence module Mc sends the detected data Db to the coincidence module Md, and the coincidence module Md sends the detected data Dc to the coincidence module Ma.

At the time illustrated in the left of FIG. 6, the coincidence module Ma holds the detected data Da besides the detected data Dc from the coincidence module Md. Consequently, the coincidence module Ma allows performing coincidence to the detected data Da, Dc. This achieves counting the number of annihilation γ-ray pairs entering in two radiation detectors corresponding to the coincidence modules Ma, Mc.

Similarly, at the time illustrated in the right of FIG. 6, the coincidence module Mb holds the detected data Db besides the detected data Dd from the coincidence module Ma. In addition, the coincidence module Mc holds the detected data Dc besides the detected data Da from the coincidence module Mb. The coincidence module Md holds the detected data Dd besides the detected data Db from the coincidence module Mc.

Accordingly, at the time illustrated in the right of FIG. 6, the coincidence module Mb allows performing coincidence to the detected data Db, Db, and the coincidence module Mc allows performing coincidence to the detected data Da, Dc. Moreover, the coincidence module Md allows performing coincidence to the detected data Db, Dd.

As noted above, among the coincidence modules Ma, Mb, Mc, and Md, one module sends the detected data to another module, the one and the other modules corresponding to the adjacent radiation detectors 1 in the detector ring 12. Similarly, such sending and receiving is repeatedly performed. As a result, the detected data received from a radiation detector corresponding to a module is sent to a module corresponding to a radiation detector located half the detector ring away. This allows performing coincidence to every combination of the radiation detectors. At this time, sending and receiving is performed between the coincidence modules Ma, Mb, Mc, and Md adjacent to each other. Moreover, one-way and chained sending of the detected data is performed so as the detected data not to be sent to its source coincidence module. Here, the coincidence modules adjacent to each other mean coincidence modules corresponding to adjacent radiation detectors 1.

The coincidence modules 21a each send the coincidence data to the coincidence data holder 22. An image generating section 25 obtains the tomographic image D of the subject M in accordance with the coincidence data held in the coincidence data holder 22.

Description will be given next of operation of the clock 19. Upon sending the time information to the coincidence unit 21, the clock 19 sends the time information to all the coincidence modules 21a collectively. Consequently, the coincidence modules 21a each ensure to recognize current time. Moreover, the coincidence modules 21a sends the obtained time information to the radiation pulse calculating modules 20a respectively corresponding to the coincidence modules 21a. The radiation pulse calculating modules 20a operate in accordance with the time information.

Similarly, upon sending the control information to the coincidence unit 21, the control information setting unit 23 sends the control information to all the coincidence module 21a collectively. This ensures to control operation of the coincidence modules 21a.

The radiation tomography apparatus 9 includes a main controller 41 configured to control each section en bloc, and a display unit 36 configured to display configured to display a radiation tomographic image. The main controller 41 has a CPU, and provides each section 16, 19, 20, 21, 23, 25 by executing various programs. The each section may be divided into a control device assigned to the section. A console 35 inputs operation by an operator to each section 16, 19, 20, 21, 23, and 25.

<Operation of Radiation Tomography Apparatus>

Description will be given next of operation of the radiation tomography apparatus. As illustrated in FIG. 1, the subject M is inserted into the detector ring 12 to conduct an inspection with the construction of Embodiment 1. Then, detection of an annihilation gamma-ray pair emitted from the subject M starts. From this time, the coincidence modules 21a start transferring the detected data mutually. The coincidence module 21a sends to another coincidence module 21a the detected data obtained from radiation pulse calculating module 20a by itself and the detected data received from another coincidence module 21a. The coincidence module 21a performs coincidence along with such operation. Then, the image generating section 25 obtains a tomographic image representing radiopharmaceutical distribution within the subject in accordance with the coincidence data generated by the coincidence unit 21. The display unit 36 displays the tomographic image, and an inspection is completed.

As noted above, the radiation tomography apparatus 9 according to the embodiment of the present invention includes a plurality of coincidence modules 21a receiving the detected data from different radiation detectors 1. The coincidence modules 21a each send and receive the detected data to and from one another, thereby sharing the detected data and counting the number of coincidence events. That is, a plurality of coincidence modules 21a cooperates to function as the coincidence unit 21 counting the number of coincidence events. In other words, when manufacturing radiation tomography apparatus 9, merely wiring the coincidence modules 21a achieves implementation of the coincidence unit 21. This allows manufacture of the radiation tomography apparatus 9 without new development of the substrate for coincidence. Consequently, the radiation tomography apparatus 9 of low costs can be provided with suppressed costs of the development.

Moreover, the coincidence modules 21a are provided in the radiation detectors 1 respectively so as to correspond to the radiation detectors 1 in a one-to-one manner. This ensures to divide a function of the coincidence device 21.

Each of the coincidence modules 21a determines the coincidence property of the detected data in accordance with the time information received from the clock 19 collectively. This allows performing coincidence in accordance with the time information with more accuracy.

Moreover, in the above embodiment, the coincidence modules 21a operate in accordance with the control information received from the control information setting unit 23 collectively. This allows immediate reflection of changing the control information to the coincidence unit 21.

The above construction is a more concrete construction of the radiation tomography apparatus 9 according to the embodiment of the present invention. The detected data received from one radiation detector 1 corresponding to one coincidence module 21a is sent to one coincidence module 21a corresponding to a radiation detector 1 located half the detector ring 12 away. This allows more accurate performance of coincidence to the modules.

The present invention is not limited to the above construction, but may be modified as under.

(1) The above construction is an apparatus for imaging a whole body of a subject. However, the present invention is limited to such the construction. The present invention is applicable to an apparatus for imaging a head of a subject, or an apparatus for breast imaging. Moreover, the present invention is applicable to an apparatus for imaging small animals. The number of radiation detectors constituting the detector ring is variable among the constructions of such the apparatus. However, the embodiment of the present invention can achieve a coincidence device by merely wiring the modules. This causes unnecessary development of a new substrate that performs coincidence.

(2) In the above construction, the radiation detectors 1 correspond to the coincidence modules 21a respectively. However, the present invention is not limited to the construction. Alternatively, a plurality of (e.g., two) radiation detectors 1 correspond to the coincidence module 21a. The radiation tomography apparatus 9 may have such a construction. In this case, the radiation pulse calculating modules 20a may correspond to the radiation detectors 1 in a one-to-one manner or to the coincidence modules 21a in a one-to-one manner. Especially, with the apparatus having a plurality of unit rings 12b, a plurality of radiation detectors 1 laminated in the z-direction may be assigned to one coincidence module 21a.

(3) In each of the foregoing embodiments, the scintillation counter crystal is composed of LYSO. Alternatively, the scintillation counter crystal may be composed of other materials, such as LGSO ($Lu_{2(1-X)}G_{2X}SiO_5$) or GSO ($Gd_2SiO_5$). This may achieve a low price radiation detector.

(4) The optical detector in each of the foregoing embodiments is constituted by a photomultiplier tube. However, the present invention is not limited to this. A photodiode, an avalanche photodiode, a semiconductor detector, or the like may be used instead of the photomultiplier tube.

Industrial Applicability

As described above, the present invention is suitable for a radiation tomography apparatus for medical use.

REFERENCE SIGN LIST 1 radiation detector
12 detector ring
19 clock
21 coincidence unit (coincidence device)
21a coincidence module (module)
23 control information setting unit (control information setting device)

The invention claimed is:
1. A radiation tomography apparatus, comprising:
a plurality of radiation detectors; and
a plurality of modules, wherein
the modules are connected to the radiation detectors respectively, and are connected to one another, and
the modules send and receive detected data outputted from the radiation detectors mutually, thereby sharing the detected data and counting the number of coincidence events.
2. The radiation tomography apparatus according to claim 1, wherein the modules are provided in the radiation detectors respectively.
3. The radiation tomography apparatus according to claim 1, further comprising:

a clock configured to send time information to the modules collectively, wherein the modules determine a coincidence property of the detected data in accordance with the time information received from the clock.

4. The radiation tomography apparatus according to claim 1, further comprising:

a control information setting device configured to send control information on coincidence to each of the modules collectively, wherein the modules operate in accordance with the control information received from the control information setting device.

5. The radiation tomography apparatus according to claim 1, wherein the detector ring is constituted by the radiation detector arranged annularly, and the detection data is sent and received between the two modules corresponding to the radiation detectors adjacent to each other, and the detected data is similarly sent and received repeatedly, whereby the detected data received from one of the radiation detector is sent to one of the module corresponding to the radiation detector located half the detector ring away.

6. The radiation tomography apparatus according to claim 1, wherein the radiation tomography apparatus is used for imaging a whole-body of the subject, for imaging a head of the subject, for breast imaging, or for small animal imaging.

7. The radiation tomography apparatus according to claim 5, wherein the modules perform one-way and chained sending of the detected data.

* * * * *